United States Patent [19]

Björk et al.

[11] Patent Number: 6,121,287

[45] Date of Patent: Sep. 19, 2000

[54] QUINOLINE DERIVATIVES

[75] Inventors: Anders Björk, Bjärred; Stig Jönsson, Lund; Tomas Fex, Lund; Gunnar Hedlund, Lund, all of Sweden

[73] Assignee: Active Biotech AB, Lund, Sweden

[21] Appl. No.: 09/352,887

[22] Filed: Jul. 14, 1999

Related U.S. Application Data

[60] Provisional application No. 60/092,966, Jul. 15, 1998.

[51] Int. Cl.$^7$ .................. A61K 31/4704; C07D 215/36; C07D 215/56; A61P 29/00; A61P 37/02
[52] U.S. Cl. ............... 514/312; 514/232.8; 544/128; 546/155
[58] Field of Search .................. 514/312, 232.8; 546/155; 544/128

[56] References Cited

FOREIGN PATENT DOCUMENTS

| | | |
|---|---|---|
| 0059698 | 9/1982 | European Pat. Off. |
| 2290786 | 1/1996 | United Kingdom. |
| 9218483 | 10/1992 | WIPO. |
| 9524195 | 9/1995 | WIPO. |
| 9524196 | 9/1995 | WIPO. |
| 9524395 | 9/1995 | WIPO. |

OTHER PUBLICATIONS

King FD. Medicinal Chemistry: Principles and Practice. The Royal Society of Chemistry. Pp. 206–208, 1994.
Japanese Abstract 07224040.
Japanese Abstract 07252228.
Talas, "Autoimmune Diseases", pp. 195–198.
Prineas, "The neuropathology of mulitple sclerosis", *Handbook of Clinical Neurology*, vol. 3, No. 47, pp. 213–257 (1985).
Karussis et al., "Treatment of secondary progressive multiple sclerosis with the immunomodulator linomide" *Neurology*, vol. 47, pp. 341–346, (1996).
Andersen et al., "Linomide reduces the rate of active lesions in relapsing–remitting multiple sclerosis" *Neurology*, vol. 47, pp. 895–900, (1996).
Kelly et al., "Polyarteritis in the Dog: A Case Report", *Vet. Rec.*, vol 92, pp. 363–366, (1973).
Harcourt, "Polyarteritis in a colony of beagles", *Vet. Rec.*, vol. 102, pp. 519–522, (1978).

*Primary Examiner*—Evelyn Mei Huang
*Attorney, Agent, or Firm*—Browdy and Neimark, P.L.L.C.

[57] ABSTRACT

The invention is related to compounds of general formula (I)

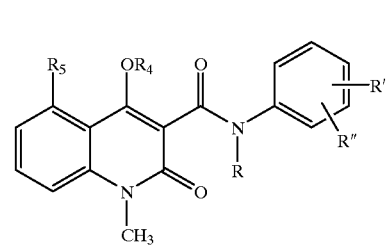

(I)

wherein R is Me, Et, n-Pr, iso-Pr, n-Bu, iso-Bu, sec.-Bu or allyl; R' is hydrogen, Me, MeO, fluoro, chloro, bromo, $CF_3$, or $OCH_xF_y$; R" is hydrogen or fluoro, with the proviso that R" is fluoro when R' is fluoro; and further when R' and R" are both hydrogen, R is not Me; $R_4$ is selected from hydrogen and pharmaceutically acceptable inorganic and organic cations; $R_5$ is selected from MeS, EtS, n-PrS, iso-PrS, MeSO, EtSO, $MeSO_2$ and $EtSO_2$; wherein x=0–2, y=1–3 with the proviso that x+y=3; and Me is methyl, Et is ethyl, Pr is propsy and Bu is butyl; and any tautomer, optical isomer and racemate thereof. The invention also relates to pharmaceutical compositions containing a compound of the general formula (I) together with a pharmaceutically acceptable carrier. Included are also processes for the preparation of the compounds of formula (I), as well as methods for the treatment of mammals suffering from diseases resulting from autoimmunity and pathological inflammation by administering of a compound having the formula (I) to said mammal.

38 Claims, No Drawings

QUINOLINE DERIVATIVES

CROSS REFERENCE TO RELATED APPLICATION

This application claims the benefit of U.S. provisional application Ser. No. 60/092,966 filed Jul. 15, 1998

FIELD OF THE INVENTION

The present invention relates to novel quinoline derivatives with a thio-substitutent incorporated into the 5-position, to methods for their preparation, to compositions containing them, and to methods and use for clinical treatment of diseases resulting from autoimmunity, such as multiple sclerosis, insulin-dependent diabetes mellitus, systemic lupus erythernatosus, rheumatoid arthritis, inflammatory bowel disease and psoriasis and, furthermore, diseases where pathologic inflammation plays a major role, such as asthma, atherosclerosis, stroke and Alzheimer's disease. More particularly, the present invention relates to novel quinoline derivatives suitable for the treatment of, for example, multiple sclerosis and its manifestations.

BACKGROUND OF THE INVENTION

Autoimmune diseases, e.g., multiple sclerosis (MS), insulin-dependent diabetes mellitus (IDDM), systemic lupus erythernatosus (SLE), rheumatoid arthritis (RA), inflammatory bowel disease (IBD) and psoriasis represent assaults by the body's immune system which may be systemic in nature, or else directed at individual organs in the body. They appear to be diseases in which the immune system makes mistakes and, instead of mediating protective functions, becomes the aggressor (1).

MS is the most common acquired neurologic disease of young adults in western Europe and North America. It accounts for more disability and financial loss, both in lost income and in medical care, than any other neurologic disease of this age group. There are approximately 250.000 cases of MS in the United States.

Although the cause of MS is unknown, advances in brain imaging, immunology, and molecular biology have increased researchers' understanding of this disease. Several therapies are currently being used to treat MS, but no single treatment has demonstrated dramatic treatment efficacy. Current treatment of MS falls into three categories: treatment of acute exacerbations; modulation of progressive disease, and therapy for specific symptoms. MS affects the central nervous system and involves a demyelination process, i.e., the myelin sheaths are lost whereas the axons are preserved. Myelin provides the isolating material that enables rapid nerve impulse conduction. Evidently, in demyelination, this property is lost. Although the pathogenic mechanisms responsible for MS are not understood, several lines of evidence indicate that demyelination has an immunopathologic basis. The pathologic lesions, the plaques, are characterised by infiltration of immunologically active cells such as macrophages and activated T cells (2).

In WO 92/18483 quinoline derivatives substituted with a $R_AS(O)_n$-group ($R_A$=lower alkyl or aryl; n=0–2) are claimed, stated to possess an inunulomodulating, anti-inflammatory and anti-cancer effect, However, said substituents are only disclosed in the 6-position of the quinoline ring.

Further, in U.S. Pat. No. 4,547,511 and in U.S. Pat. No. 4,738,971 and in EP 59,698 some derivatives of N-aryl-1, 2-dihydro-4-substituted-1-alkyl-2-oxo-quinoline-3-carboxamide are claimed as enhancers of cell-mediated immunity. The compound

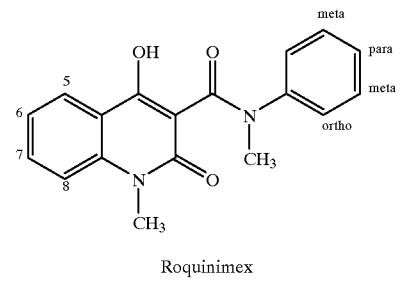

Roquinimex known as roquinimex (Merck Index 12th Ed., No. 8418) belongs to this series of compounds. Roquinimex has been reported to have multiple immunomodulatory activities not accompanied with general immunosuppression.

Furthermore, in U.S. Pat. No. 5,580,882, U.S. Pat. No. 5,594,005, WO 95/24195 and WO95/24196 quinoline-3-carboxamide derivatives are claimed to be useful in the treatment of conditions associated with MS, type I diabetes, inflammatory bowel disease and psoriasis, respectively. The particular preferred compound is roquinimex.

The substitution, i.e, type and pattern, of the above compounds, specifically mentioned in the prior art, places them outside the scope of the present invention.

In clinical trials comparing roquinimex to placebo, roquinimex was reported to hold promise in the treatment of conditions associated with MS (3, 4). There are, however, some serious drawbacks connected to some quinoline-3-carboxamide derivatives. For example, it has been found that roquinimex is teratogenic in the rat, and induces dose-limiting side effects in man, e.g., a flu-like syndrome, which prevents from using the full clinical potential of the compound.

DESCRIPTION OF THE INVENTION

A primary objective of the present invention is to provide structurally novel quinoline compounds which by virtue of their pharmacological profile, with high potency in experimental models and low level of side-effects, are considered to be of value in the treatment of disease resulting from autoimmunity and pathologic inflammation. Examples of such diseases are multiple sclerosis, insulin-dependent diabetes mellitus, systemic lupus erythematosus, rheumatoid arthritis, inflammatory bowel disease and psoriasis and other diseases where inflammation plays a major role, such as asthma, atherosclerosis, stroke and Alzheimer's disease. More particularly, the present invention relates to novel quinoline derivatives suitable for the treatment of, for example, multiple sclerosis and its manifestations.

The term "treatment" as used herein includes prophylaxis as well as relieving the symptoms of disease.

It has now surprisingly been found that the new and novel compounds of general formula (I)

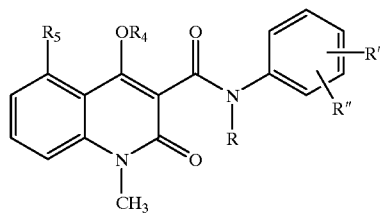

(I)

wherein
R is selected from Me, Et, n-Pr, iso-Pr, n-Bu, iso-Bu, sec.-Bu and allyl;
R' is selected from hydrogen, Me, MeO, fluoro, chloro, bromo, $CE_3$, and $OCH_xF_y$;
R" is selected from hydrogen and fluoro, with the proviso that R" is fluoro when R' is fluoro and further provided that when R' and R" are both hydrogen, R is not Me;
$R_4$ is selected from hydrogen and pharmaceutically acceptable inorganic cations, such as sodium, potassium and calcium, and organic cations such as monoethanolamine, diethanolamine, dimethylaminoethanol, morpholine and the like;
$R_5$ is selected from MeS, EtS, n-PrS, iso-PrS, MeSO, EtSO, $MeSO_2$ and $EtSO_2$;
wherein x=0–2,
y=1–3 with the proviso that
x+y=3; and
Me is methyl, Et is ethyl, Pr is propyl and Bu is butyl; are unexpectedly effective and specific in the treatment of individuals suffering from autoimmune and inflammatory diseases.

The compounds of general formula (I) may exist in different tautomeric forms and all such forms where such forms exist are included herein. Also optical isomers and racemates of the compounds of general formula (I) where such forms exist are included herein.

In a preferred embodiment of the invention $R_4$ is selected from hydrogen and sodium,
$R_5$ is selected from MeS, and EtS,
R is selected from methyl, ethyl and propyl,
R' is selected from methoxy, fluoro, chloro and trifluoromethyl when R" is hydrogen, and R is methyl;
R" is selected from meta'- and para-fluoro when R' is ortho-fluoro and R is methyl; and
R' and R" are both hydrogen when R is ethyl and propyl.

Among the most preferred compounds of general formula (I) according to the present invention are:
N-ethyl-N-phenyl- 1,2-dihydro-4-hydroxy-5-thiomethyl-1-methyl-2-oxo-quinoline-3-carboxamide,
N-n-propyl-N-phenyl-1,2-dihydro4-hydroxy-5-thiomethyl-1-methyl-2-oxo-quinoline-3-carboxamide,
N-methyl-N-(4-methoxy-phenyl)-1,2-hydro-4-hydroxy-5-thiomethyl- 1-methyl-2-oxo-quinoline-3-carboxamide,
N-methyl-N-4-chloro-phenyl)-1,2-dihydro-4-hydroxy-5-thiomethyl-1-methyl-2-oxo-quinoline-3-carboxamide,
N-methyl-N-(4-trifluoromethyl-phenyl)-1,2-dihydro-4hydroxy-5-thiomethyl-1-methyl-2-oxo-quinoline-3-carboxamide,
N-methyl-N-(2,4-difluoro-phenyl)-1,2-dihydro4-hydroxy-5-thiomethyl- 1-methyl-2-oxo-quinoline3-carboxamide,
N-methyl-N-(2,5-difluoro-phenyl)-1,2-dihydro-4hydroxy-5-thiomethyl--methyl-2-oxo-quinoline-3-carboxamide,
N-ethyl-N-phenyl-1,2-dihydro-4-hydroxy-5-methylsulphinyl- 1-methyl-2-oxo-quinoline-3-carboxamide,
N-n-propyl-N-phenyl-1,2-dihydro-4-hydroxy-5-methylsulphinyl-1-methyl-2-oxo-quinoline-3-carboxamide, and
N-methyl-N-(2,4-difluoro-phenyl)-1,2-dihydro4-hydroxy-5- methylsulphinyl-methyl-2-oxo-quinoline-3-carboxamide.

Several spontaneously occurring autoimmune diseases in man have experimental models that are spontaneously occurring in certain strains of laboratory animals or can be induced in laboratory animals by immunisation with specific antigen(s) from the target organ.

Experimental autoimmune encephalomyelitis (CAM) as a model for autoimmune inflammatory diseases of the central nervous system (CNS) has been the most widely used model for the human disease multiple sclerosis.

Autoimmunity to type II collagen can experimentally be induced in certain strains of mice or rats and may lead to the development of polyarthritis. The collagen induced arthritis has several features in common with the human disorder rheumatoid arthritis.

The hallmark of asthma in humans is an increased reactivity of the airways to a range of chemical and physical stimuli. It is now widely accepted that products released from inflammatory cells, e.g., activated eosinophils, compromise epithelial integrity and promote bronchial hyperresponsiveness. The murine model of ovalbumin (OA)-induced lung inflammation is dominated by the temporally regulated influx of lymphocytes and eosinophils into the bronchial lumen.

Roquinimex has been found to induce the Beagle Pain Syndrome (BPS) (5, 6) in different breeds of beagle dogs. The disease is reflected by clinical and laboratory manifestations justifying BPS as a model for the flu-like syndrome induced by roquinimex in man.

The compounds of general formula (I) were assayed for inhibition of acute experimental autoimmune encephalomyelitis (aEAE) in mice, Roquinimex was used as treatment control and showed a more than 50% inhibition at ≧5 mg/kg. Surprising and unexpected results were obtained when introducing proper substitution in the 5-position of the quinoline ring. In comparison with roquinimex, the potency of the 5-thiomethyl substituted compound was increased a 100-fold. Corresponding substitution in the 6-position resulted in less active compounds, as shown in the examples. Furthermore, proper aromatic substitution of the 3-carboxamide moiety of the compounds of general formula (I) significantly reduced or even abolished the side-effects, i.e., the teratogenic effects and the BPS, of roquinimex. Thus, physicochemical properties of the 5-substituent in the quinoline moiety and the ortho-, meta-and/or, in particular, the para- substituent in the 3-carboxamide moiety are of major importance for an improved risk/benefit ratio in comparison with roquinimex. Also replacement of the methyl group on the carboxamide nitrogen with a higher alkyl group significantly reduced the side effects. Hence, the compounds of formula (I) have surprisingly been found to be both chemically and pharmacologically different from those drugs hitherto suggested for the treatment of MS and its manifestations.

All embodiments of the invention as disclosed in the claims are herewith included in the specification.

The following examples are intended to illustrate the invention without restricting the scope thereof.

The compounds of general formula (I) may be prepared by methods known in the literature and the following methods:

Method A:

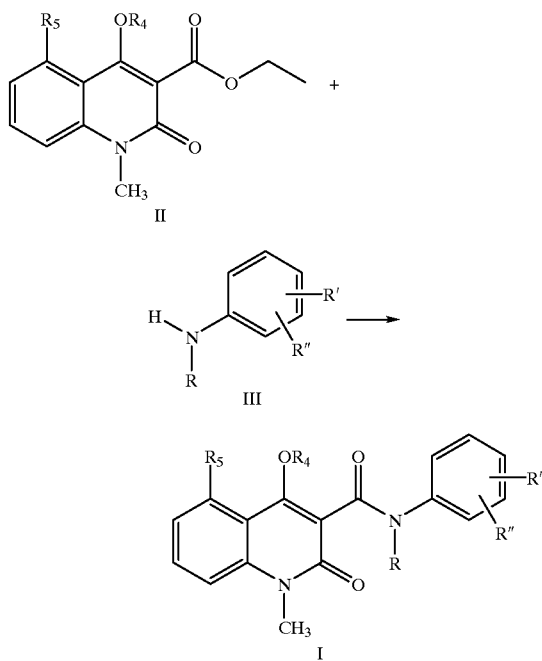

The compounds of general formula (I) may be prepared by known methods and, for example, as shown above, by reaction of an ester derivative of the quinoline carboxylic acid with an aniline in a suitable solvent such as toluene, xylene and the like. General methods for preparation of the quinoline carboxylic acid ester derivatives of formula (II) are described below. N-alklated anilines of formula (El are commercially available or blown from literature, e.g., in Johnstone et al, J. Chem. Soc. 1969, 2223–2224. Compounds falling within the scope of formula (III) may be prepared by methods, which are generally analogous to those of said literature.

Method B:

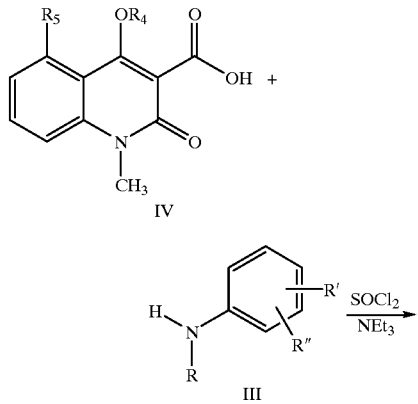

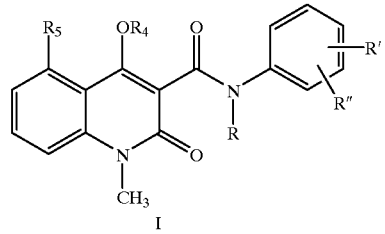

The compounds of formula (I) may also be prepared by reaction of a quinoline carboxylic acid of formula (IV) with an aniline of formula (III). Various coupling reagents known in the art may be used, e.g., carbodiimides known from literature in U.S. Pat. No. 4,547,511. One suitable coupling method utilises thionyl chloride in the presence of diethylamine and a suitable solvent such as dichloromethane. This method may be used in instances when direct coupling between ester and aniline does not work, e.g., when the aniline contains electron withdrawing substituents. The quinoline carboxylic acids of formula (IV) may be obtained from the corresponding esters of formula (H) by acidic hydrolysis as described below.

EXAMPLE 1
1.2-Dihydro-4-hydroxy-5-thiomethyl-1-methyl-2-oxo-quinoline-3-carboxylic acid ethyl ester 2,6-Difluorobenzonitrile (13.2 g, 0.10 mol) was slowly added to a solution of sodium sulphide nonahydrate (26.4 g, 0.11 mol) in 300 ml of N,N-dimethylformamlde. After stirring the solution overnight, it was worked up with ether and 1 M hydrochloric acid. The ether phase was treated with 1 h sodium hydroxide and then the aqueous phase was acidified with hydrochloric acid followed by ether extraction. The ether phase was carefully dried and the solvent removed. The residue (12.5 g) was added in portions to a solution of sodium hydride (3.8 g, 0.12 mol) in 300 ml of cold N,N-dimethylformamide, followed by addition of methyl iodide (0 ml, 0.15 mol). The mixture was stirred for 6 hours at ambient temperature, poured onto ice-water and the resulting precipitate, 2-fluoro-6-thiomethyl-benzonitrile, filtered off and dried. The precipitate was warmed at 40° C. in 200 ml of anhydrous methylamine in an autoclave for 2 days, The excess methylamine was allowed to evaporate and the resulting yellow solid (16 g) was dissolved in 200 ml of dichloromethane together with 4-aminopyridine (0.1 g, 0.001 mol) and triethylamine (5.6 ml, 0.045 mol). To this chilled solution was slowly added ethyl malonyl chloride (15 g, 0.10 mol). The solution was stirred for 4 hours and worked up to give a yellowish syrup. The syrup was dissolved in 100 ml of anhydrous ethanol, and sodium methoxide (7.5 g, 0.14 mol) was added. After 1 hour, the solvent was removed and the residue worked up with dichloromethane and water, The quinoline derivative formed was suspended in 250 ml of chilled anhydrous tehydrofuran, and sodium hydride (5.3 g. 0.175 mol) was slowly added, followed by addition of methyl iodide (13 ml, 0.21 mol). The mixture was heated under reflux for 6 hours, quenched with water and worked up with diethyl ether, The solvents were removed and the residue (17.3 g) dissolved in a mixture of 100 ml of ethanol and 5 ml of conc. hydrochloric acid. The solution was warmed at 80° C. for 4 hours, cooled and the precipitate was collected and purified by silica gel chromatography to give the title compound (4 g).

1H NMR (CDCl$_3$) δ1.46 (3H, t), 2.48 (3H, s), 3.62 (3H, s), 4.48 (211, q), 6.98 (1H, d), 7.05 (1H, d), 7.52 (1H, t), 15.5 (1H, s).

EXAMPLE 2

N-Ethyl-N-phenyl-1,2-dihydro-4-hydroxy-5-thiomethyl-1-methyl-2-oxo-quinoline-3-carboxamide N-Ethylaniline (3.0 g, 0.025 mol) was dissolved in 80 ml of toluene and about 30 ml of the solvent was distilled off in order to obtain a dry solution. 1,2-Dihydro-4-hydroxy-5-thiomethyl-1-methyl-2-oxo-quinoline-3-carboxylic acid ethyl ester (2.9 g, 0.01 mol) was added to the boiling solution. The ethanol formed during the reaction was distilled off together with some toluene for about 4 hours, The mixture was cooled to room temperature. The precipitate was collected, washed with cold toluene and hexane and dried to give the title compound (2.1 g), yield 57%.

1H NMR (CDCl$_3$) δ1.22 (3H, t), 2.47 (311, s), 3.35 (311, s), 3.96 (2H, q), 7.06 (1H, d), 7.09 (1H, d), 7.14–7.26 (5H, m), 7.45 (11H, t). 13C NMR (CDCl$_3$) δ13.0 (CH3), 18.5 (C013), 29.7 (0113), 45.4 (CH2), 105.2 (C), 112.1 (CH), 113.1 (C), 121.8 (CH), 126.7 (CH), 126.9 (CH), 128.5 (CH), 131.4 (CH), 138.7 (C), 142.3 (C), 158.5 (C), 165.5 (C), 168.4 (C).

ESI MS/MS [M+H]$^+$369, fragments 248 and 122.

In essentially the same manner the following compounds were obtained from the corresponding starting materials:

N-allyl-N-phenyl-1,2-dihydro-4-hydroxy-5-thiomethyl-1- methyl-2-oxo-quinoline-3-carboxamide, N-methyl-N-phenyl-1,2-dihydro-4-hydroxy-5-thiomethyl-1-methyl-2-oxo-quinoline-3-carboxamide (not included in the claims), 1H NMR (CDCl$_3$) δ2.45 (3H, s), 3.38 (3H, s), 3.48 (3H, s), 7.04 (1H, d), 7.06 (1H, d), 7.11–7.25 (5H, m), 7.43 (1H, t).

13C NMR (CDCl$_3$) 6 18.3 (CH3), 29.8 (CH3), 38.4 (CH3), 104.6 (C), 112.0 (CH), 113.2 (C), 121.5 (CH), 125.7 (CH), 125.7 (CH), 126.8 (CH), 128.7 (CH), 128.7 (CH), 131.5 (CH), 139.1 (C), 142.3 (C), 144.2 (C), 158.7 (C), 166.0 (C), 169.1 (C). ESI MS/MS [M+H]$^+$355, fragments 248 and 108.

N-n-propyl-N-phenyl-1,2-dihydro-4-hydroxy-5-thiomethyl 1-methyl-2-oxo-quinoline-3-carboxamide, N-methyl-N-(4-chloro-phenyl)-1,2-dihydro-4-hydroxy-5-thiomethyl-1-methyl-2-oxo-quinoline-3-carboxamide, N-ethyl-N-(4-methoxy-phenyl)- 1,2-dihydro-4-hydroxy-5-thiomethyl-1-methyl-2-oxo-quinoline-3-carboxamide, N-methyl-N-(4methoxy-phenyl)-1,2-dihydro-4-hydroxy-5-thiomethyl-1 -methyl-2-oxo-quinoline-3-carboxamide, 1H NMR (CDCl$_3$) δ2.43 (3H, s), 3.39 (3H, s), 3.40 (3H, s), 3.72 (3H, s), 6.72 (2H, broad signal), 7.01–7.21 (4H, m), 7.44 (1H, t). 13C NMR (CDCl$_3$) δ18.6 (CH3), 29.9 (CH3), 38.4 (CH3), 55.4 (CH3), 112.3 (CH), 113.3 (C), 113.9 (CH), 123 (CH), 127.1 (CM), 131.4 (CH), 137 (C), 138 (C), 142.3 (C), 158.2 (C), 158.7 (C), 169 (C).

ESI MS/MS [M+H]$^+$385, fragments 248 and 138.

EXAMPLE 3

N-Methyl-N-phenyl-1,2-dihydro-4-hydroxy-5-methylsulphinyl-1-methyl-2-oxo-quinoline-3-carboxamide (not included in the claims)

N-Methyl-N-phenyl- 1,2-dihydro-4-hydroxy-5-thiomethyl-1 -methyl-2-oxo-quinoline-3-carboxamide (0.14 g, 0.32 mmol) was dissolved in 5 ml of dichloromethane. The solution was cooled in an ice-bath and 70% 3-chloroperoxybenzoic acid (83.3 mg, 0.34 mmol) dissolved in 2 ml of dichloromethane was slowly added. After stirring for 4 hours, the solution was triturated with 3 ml of heptane followed by recrystallization of the preciptate from ethyl acetate - pentane to give the title compound (25 mg).

1H NMR (CDCl$_3$) δ2.79 (3H, s), 3.39 (3H, s), 3.50 (3H, s), 7.15–7.29 (5H, m), 7.35 (1H, d), 7.75 (1H, t), 8.06 (1H, d).

ESI MS/MS [M+H]$^+$371, fragment 264.

In essentially the same manner the following compound was obtained from the corresponding starting materials:

N-ethyl-N-phenyl-1,2-dihydro-4-hydroxy-5-methylsulphinyl- 1 -methyl-2-oxo-quinoline-3-carboxamide, N-n-propyl-N-phenyl-1,2-dihydro-4-hydroxy-5-methylsulphinyl-1-methyl-2-oxo-quinoline-3-carboxamide, N-methyl-N-(4-methoxy-phenyl)-1,2-dihydro-4hydroxy-5-methylsulphinyl-1-methyl-2-oxo-quinoline-3-carboxamide, N-methyl-N-(4- chloro-phenyl)- I ,2-dihydro-4-hydroxy-5-methylsulphinyl- 1 -methyl-2-oxo-quinoline-3-carboxamide.

EXAMPLE 4

N-Methyl-N-(4-trifluoromethyl-phenyl)-1,2-dihydro-4-hydro-5-thiomethyl-1-methyl-2-oxo-quinoline-3-carboxamide (Method B).

To an ice-cold solution of 1,2-dihydro-4-hydroxy-5-thiomethyl- -methyl-2-oxo-quinoline-3-carboxylic acid (8.5 g, 0.032 mol), trimethylamine (5.5 ml, 0.11 mol) and 4-trifluoromethyl-N-methylaniline (6.1 g, 0.035 mol) in 150 ml of methylene chloride was added dropwise during 0.5 hours a solution of thionyl chloride (3.0 ml, 0.042 mol) in 10 ml of methylene chloride. The stirring was continued at 40° C. for 4 hours. The solution was diluted with 10 ml of methylene chloride, washed with cold 1 M sulphuric acid and extracted with 1 M sodium hydroxide. The pH of the aqueous phase was adjusted to 8–8.5, it was clarified by filtration and then acidified with hydrochloric acid solution to pH 4. On standing a crystalline precipitate was formed which was filtered off, washed with water and dried to give the title compound (8.5 g) yield 72%, In essentially the same manner the following compounds were obtained from the corresponding starting materials:

N-ethyl-N-(4-trifluoromethyl-phenyl)-1,2-dihydro-4-hydroxy-5-thiomethyl-1-methyl-2-oxo-quinoline-3-carboxamide, N-methyl-N-(4-trifluoromethoxy-phenyl)-1,2-dihydro-4-hydroxy-5-thiomethyl-1-methyl-2-oxo-quinoline-3-carboxamide, N-ethyl-N-(2,4-difluoro-phenyl)- 1,2-dihydro-4-hydroxy-5-thiomethyl-1-methyl-2-oxo-quinoline-3-carboxamide, N-methyl-N-(2,4-difluoro-phenyl)-1,2-dihydro-4-hydroxy-5-thiomethyl-methyl-2-oxo-quinoline-3-carboxamide, 1H NMR (CDCl$_3$) δ2.46 (3H, s), 3.33 (3H, s), 3.37 (3H, s), 6.63(1H, broad), 6.83 (1H, broad), 6.95–7.15 (3H, m broad), 7.45 (1H, t). 13C NMR (CDCl$_3$) δ17.7 (CH3), 29.8 (CH3), 37.2 (CH3), 103.2 (C), 104.6+104.8+105.0 (CH), 110.5 (CH), 111.3 (CH), 112.7 (C), 120.1 (CH), 128.4 (C), 128.5 (CH), 131.9 (CH), 140.6 (C), 142.6 (C), 156.9+157.0+159.0+159.1 (C), 158.4 (C), 160.6+162.6 (C), 168.0 (C), 170.4 (C); some peaks are multiplets due to F-coupling. ESI MS/MS [M+H)]$^+$391, fragment 248.

N-methyl-N-(2,5-difluoro-phenyl)-1,2-dihydro4-hydroxy-5-thiomethyl-1-methyl-2-oxo-quinoline-3-carboxamide and N-methyl-N-(4-trifluoromethyl-phenyl)-1,2-dihydro-4-hydroxy-5-methylsulphinyl-1-methyl-2-oxo-quinoline-3-carboxamide and N-methyl-N-(2,4-difluoro-phenyl)-1,2-dihydro-4-hydroxy-5- methylsulphinyl-methyl-2-oxo-quinoline-3-carboxamide.

Pharmacological methods

Acute experimental autoimmune encephalomyelitis (aEAE)

STUN female mice, 8 weeks of age, were used for the experiments. Mouse spinal cord homogenate (MSCH) was obtained from 8 to 12 weeks-old C57BV6 female mice. The tissue was homogenised on ice and diluted in cold PBS. Incomplete Freund's containing 1 mg/ml M. tuberculosis hominis H37Ra was emulsified with an equal volume of MSCH to give a final concentration of 10 mg/ml of MSCH. The inoculum volume of 0.1 ml was injected intradermally at the base of the tail. Pertussis toxin was injected i.p. at day 0 and 3 after inmmunization. Treatment was given per os daily either at day 3 to 12 post-immunization or days 3 to 7 and 10 to 12. Control animals received saline. The animals, eight per dose group, were scored for clinical signs of paralytic disease on a scale from 0 to 5 in the following way: 0, normal; 1, limp tail; 2, hind limb paresis; 3 hind limb paralysis and limp foreleg; 4, bilateral hind and fore limb paralysis; 5, death. Clinical scores were monitored at day 7 and daily from day 9 until the end of the experiment at day 14. Treatment effects were calculated as percent inhibition of clinical scores compared to saline treated controls.

Collagen induced arthritis

DBA/1 male mice between 8 to 10 weeks of age were used for the experiments On day 0 the mice were immunized intradermally at the base of the tail with bovine type 11 collagen (100 4g/mouse) in Freund's complete adjuvant. The treatment was given per os daily on days 3 to 7, 10 to 14, 17 to 21, 24 to 28 and 31 to 35. Fifteen days after immunization mice were inspected for signs of arthritis. The animals were inspected three times a week. Every second or third day individual paws of the arthritic animals were scored by a scale from 0–4 (0=no arthritis, 1=arthritis in one of the interphalangeal, metatusophalangeal or intercarpal joints, 2=two arthritic joints, 3=three arthritic joints, 4=as in 3 but with more severe redness and swelling of the paw). The score for each paw was added to give a maximal attainable score of 16 for each mouse.

Ovalbumin-induced lung inflammation

C57B31 6 female mice between 10 to 14 weeks of age were used for the experiments, 10 mice /group. The mice were sensitized with ovalbumin (OA) in aluminium hydroxide in a volume of 0.2 ml inoculated ip. Treatment was given at day 0 to day 16. Control mice received saline. Fourteen days after the OA sensitization mice were exposed for 20 minutes to an aerosol of 1.5% w/v of OA in saline produced by a nebulizer. Vehicle-challenged control mice were exposed to saline. Seventy-two hours after OA/vehicle challenge, mice were anaesthetised and bronchoalveolar lavage was performed by instilling 0.5 ml ice-cold phosphate buffered saline (PBS) into the lungs twice. Total cell counts were determined and differential counts were made based on identification of eosinophils, monocyteslalveolar macrophages, lymphocytes and neutrophils. Eosinopbil infiltration into the lung tissue was evaluated by histochemical methods on frozen lung sections using diaminobenzidine tetrahydrochioride (DAB).

Teratogenic Effects in the Rat

The compounds were administrated subcutaneously to female rats during pregnancy, i.e., day 8 to 14 of pregnancy. The rats were caesarean sectioned and necropsied on day 20 after fertilization. The foetuses were examined for external and internal abnormalities.

Beagle Pain Syndrome (BPS)

The compounds were administrated intravenously to beagle dogs. The dosage was given for five consecutive days. The dogs were evaluated for clinical and laboratory signs of the pain syndrome, e.g., fever, increased errocyte sedimentation rate (ESR), alkaline phosphate (AP), induction of acute phase proteins and vasculitis Among preferred compounds are N-ethyl-N-phenyl-1,2-dihydro-4-hydroxy-5-thiomethyl-1-methyl-2-oxo-quinoline-3-carboxamide and N-methyl-N-(2,4-difluoro-phenyl)- 1,2-dihydro-4-hydroxy-5-thiomethyl-1-methyl-2-oxo-quinoline-3-carboxamide hereinafter called Compound A and B, respectively. N-ethyl-N-phenyl-1,2-dihydro-4-hydroxy-6-thiomethyl-1-methyl-2-oxo-quinoline3-carboxamide and N-methyl-N-(2,4difluoro-phenyl)-l,2-dihydro-4-hydroxy-6-thiomethyl-1-methyl-2-oxo-quinoline-3-carboxamide are included as reference compounds hereinafter called Compound C and D, respectively:

| | % aEAE Inhibition | | | |
|---|---|---|---|---|
| Dose, mg/kg p.o. | Compound A (invention) | Compound B (invention) | Compound C | Compound D |
| 0.04 | 28 | | 0 | |
| 0.2 | 49 | 67 | 23 | 0 |
| 1 | | 97 | | 66 |

Teratogenic Effects in the Rat

While in a dose of 6 mg/kg/day N-methyl-N-phenyl-1,2-dihydro-4-hydroxy-5-thiomethyl-1-methyl-2-oxo-quinoline-3-carboxamide was found to be teratogenic in the rat, Compound A and B were found to be non-teratogenic.

Effective quantities of the compounds of formula (I) are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules, and powders prepared for oral administration, aerosols for inhalation, sterile solutions for parental administration, suppositories for rectal administration or suitable topical formulations. Conventional procedures for the selection and preparation of suitable pharmaceutical formulations are described, for example, in "Pharmaceuticals—The Science of Dosage Form Design", M. B. Aulton, Chuhill Livingstone, 1988.

A suitable daily dose for use in the treatment of MS is contemplated to vary between 0.0005 mg/kg to about 10 mg/kg body weight, in particular between 0.005 mg/kg to 1 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease of administration of the drug are contemplated. The pharmaceutical composition may also contain additional therapeutically useful substances other than a compound of formula (I).

References

1. Talal, N.: Autoimmune diseases, In: Roitt, I. M. and Delves, P. J. (eds.) Encyclopedia of Immunology, pp. 195–198, Academic Press, 1992.
2. Prineas, J. W.: The neuropathology of multiple sclerosis. In: Koetsier, 3.C. (ed.) Handbook of Clinical Neurology, pp. 213–257. Elsevier Science Publ., Amsterdam, 1985.
3. Karussis, D. M. Meiner, Z., Lehmann, D. et al. Treatment of secondary progressive multiple sclerosis with the immunomodulator Linomide. Neurology 47: 341–346, 1996.
4. Andersen, O., Lycke, J., Tollesson, P. O. et al. Linomide reduces the rate of active lesions in relapsing-remitting multiple sclerosis. Neurology 47: 895–900, 1996.
5. Kelly, D. F., Grüsell, C. S. G. and Kenyon, C. J. Polyarthritis in the dog: A case report. Vet Record 92: 363–366, 1973.
6. Harcourt, R. A. Polyarterites in a colony of beagles. Vet Record 102: 519–522, 1978.

We claim:

1. A compound of general formula (I)

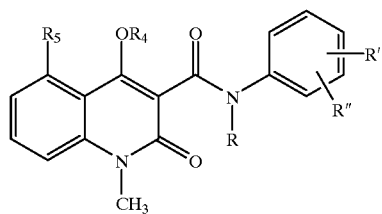

(I)

wherein
R is selected from the croup consisting of ME, Et, n-Pr, iso-Pr, n-Bu, sec.-Du and allyl;
R' is selected from the group consisting of hydrogen, Me, MeO, fluoro, chloro, bromo, $CF_3$, and $OCH_xF_y$;
R" is selected from hydrogen or fluoro, with the proviso that R" is fluoro when R' is fluoro and further provided that when R' and R' are both hydrogen R is not Me;
$R_4$ is selected from the group consisting of hydrogen and pharmaceutically acceptable inorganic and organic cations;
$R_5$ is selected from the group consisting of MeS, EtS, n-PrS, iso-PrS, MeSO, and EtSO,
wherein
x=0–2,
y=1–3 with the proviso that
x+y=3; and
Me is methyl, Et is ethyl, Pr is propyl and Bu is butyl;
or a tautomer, or an optical isomer or racemate thereof.

2. The compound according to claim 1 wherein the pharmaceutically acceptable inorganic cation is derived from sodium, potassium, or calcium, and the organic cation is derived from monoethanolamine, diethanolamine, dimethylaminoethanol, or morpholine.

3. The compound according to claim 1 wherein $R_5$ is MeS, or EtS.

4. The compound according to claim 1 wherein R is methyl when at least one of R' and R" is not hydrogen.

5. The compound according to claim 1 wherein R is ethyl or propyl ad R' and R" are both hydrogen.

6. The compound according to claim 1, N-n-propyl-N-phenyl-1,2-dihydro-4-hydroxy-5-thiomethyl-4 -methyl-2-oxo-quinoline-3-carboxamide.

7. The compound according to claim 1, N-methyl-N-(4-trifluoromethyl-phenyl)-1,2-dihydro-4-hydroxy-5-thiomethyl-1-methyl-2-oxo-quinoline-3-carboxamide.

8. The compound according to claim 1, N-methyl-N-(2, 4-difluoro-phenyl)- 1,2-dihydro-4-hydroxy-5-thiomethyl-1-methyl-2-oxo-quinoline-carboxamide.

9. The compound according to claim 1, N-methyl-N-(2, 5-difluoro-phenyl)-1,2-dihydro-4-hydroxy-5-thiomethyl-1-methyl-2-oxo-quinoline-3-carboxamide.

10. The compound according to claim 1, N-n-propyl-N-phenyl-1,2-dihydro-4-hydroxy-5-methylsulphinyl-1-methyl-2-oxo-quinoline-3-carboxamide.

11. A pharmaceutical composition compressing an active ingredient a pharmaceutically effective amount of a compound having the formula (I) according to claim 1 together with a pharmaceutically acceptable carrier.

12. The pharmaceutical composition according to claim 11 in a dosage form suitable to be used as therapeuticum in a daily dose of the active substance of 0.0005 mg/kg to about 10 mg/kg body weight.

13. A process for the manufacturing of a compound of the formula (I) of claim 1 comprising (A) reacting an ester derivative of quinoline carboxylic acid of formula (II)

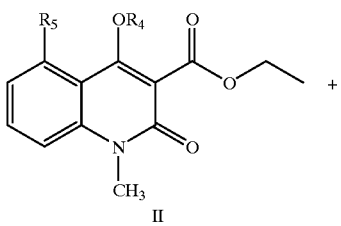

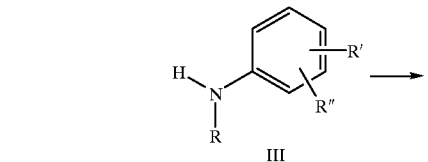

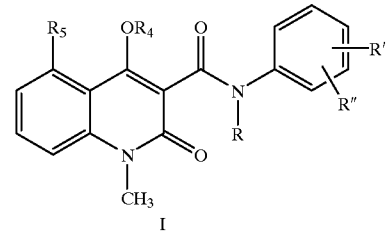

with an aniline of formula (iMi), in a solvent or (B) reacting an quinoline carboxylic acid of the formula (IV) with an aniline of the formula (III),

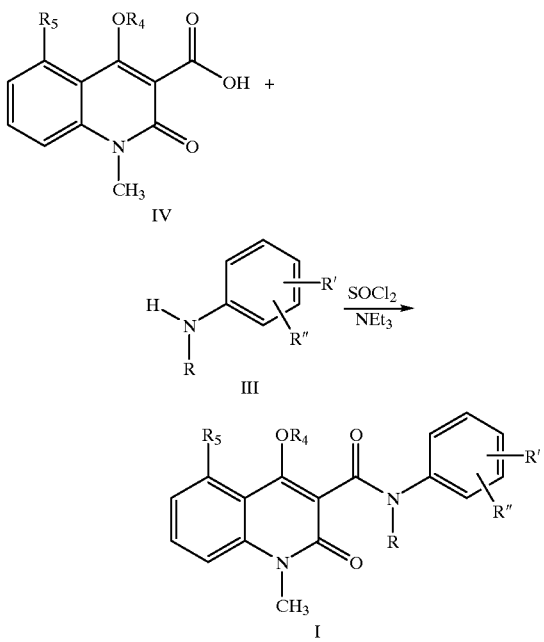

using a coupling reagent, in the presence of triethylamine and a solvent.

14. A method of treating a mammal suffering from a pathologic inflammation or a disease resulting from autoimmunity comprising administering to said mammal in need thereof a therapeutically effective amount of a compound having the formula

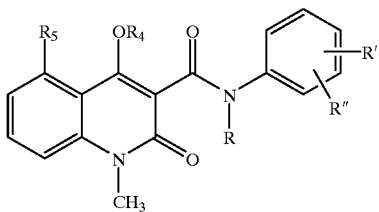

wherein

R is selected from the group consisting of ME, Et, n-Pr, iso-Pr, n-Bu, sec.-Bu and allyl;

R' is selected from the group consisting of hydrogen, Me, MeO, fluoro, chloro, bromo, $CF_3$, and $OCH_xF_y$;

R" is selected from hydrogen or fluoro, with the proviso that R" is fluoro when R' is fluoro and further provided that when R' and R" are both hydrogen, R is not Me;

$R_4$ is selected from the group consisting of hydrogen and pharmaceutically acceptable inorganic and organic cations;

$R_5$ is selected from the group consisting of MeS, EtS, n-PrS, iso-PrS, MeSO, and EtSO;

wherein x=0–2, y=1–3 with the proviso that x+y=3; and

Me is methyl, Et is ethyl, Pr is propyl and Bu is butyl; or a tautomer, optical isomer or racemate thereof.

15. The method according to claim 14 wherein the pharmaceutically acceptable inorganic cation is derived from sodium, potassium, or calcium, and the organic cation is derived from monoethanolamine, diethanolamine, dimethylaminoethanol, or morpholine.

16. The method according to claim 14 wherein $R_5$ is MeS or EtS.

17. The method according to claim 14, wherein R is methyl when at least one of R' and R" is not hydrogen.

18. The method according to claim 14, wherein R is ethyl or propyl and R' and R" are both hydrogen.

19. The method according to claim 14, N-n-propyl-N-phenyl-1,2-dihydro4-hydroxy-5-thiomethyl-1-methyl-2-oxo-quinoline-3-carboxamide.

20. The method according to claim 14, N-methyl-N-(4-trifluoromethyl-phenyl)-1,2-dihydro4-hydroxy-5-thiomethyl-1-methyl-2-oxo-quinoline-3-carboxamide.

21. The method according to claim 14, N-methyl-N-(2, 4-difluoro-phenyl)-1,2-dihydro-4-hydroxy-5-thiomethyl-1-methyl-2-oxo-quinoline-3-carboxamide.

22. The method according to claim 14, N-methyl-N-(2, 5difluoro-phenyl)-1,2-dihydro4-hydroxy-5-thiomethyl-1-methyl-2-oxo-quinoline-3-carboxamide.

23. The method according to claim 14, N-n-propyl-N-phenyl-1,2-dihydro-4-hydroxy-5-methylsulphinyl-1-methyl-2-oxo-quinoline-3-carboxamide.

24. The method according to claim 14 of treating mammals suffering from multiple sclerosis (MS).

25. The method according to any of claim 14 of treating a mammal suffering from insulin-dependent diabetes mellitus (IDDM).

26. The method according to claim 14 of treating a mammal suffering from systemic lupus erythematosus (SLE).

27. The method according to claim 14 of treating a mammal suffering from rheumatoid arthritis (RA).

28. The method according to claim 14 of treating a mammal suffering from inflammatory bowel disease (IBD).

29. The method according to claim 14 of treating a mammal suffering from psoriasis.

30. The method according to claim 14 of treating mammals suffering from inflammatory respiratory disorder, such as asthma.

31. The method according to claim 14 of treating a mammal suffering from atherosclerosis.

32. The method according to 14 of treating a mammal suffering from stroke.

33. The method according to claim 14 of treating a mammal suffering from Alzheimer's disease.

34. The method according to claim 14 administered in a daily dose of said compound of 0.0005 mg/kg of body weight to about 10 mg/kg body weight.

35. The method according to claim 14 administered in a daily dose of said compound of 0.005 mg/kg of body weight to about 1 mg/kg body weight.

36. The method of claim 30 wherein said inflammatory respiratory disorder is asthma.

37. The process of claim 13 wherein, in reaction (A) said solvent is toluene or xylene; or in reaction (B) said coupling agent is a carbodiimide or thionyl chloride, and said solvent is dichloromethane.

38. The compound of claim 1 which is N-methyl-N-(4-chloro-phenyl)-1,2-dihydro-4-hydroxy-5-thiomethyl-1-methyl-2-oxo-quinoline-3-carboxamide.

* * * * *

UNITED STATES PATENT AND TRADEMARK OFFICE
CERTIFICATE OF CORRECTION

PATENT NO.   : 6,121,287
DATED        : September 19, 2000
INVENTOR(S)  : Bjork et al.

It is certified that error appears in the above-identified patent and that said Letters Patent is hereby corrected as shown below:

Title page,
Item [57], ABSTRACT,
Line 4, delete "brorno" and insert therefor -- bromo --;
Line 13, delete "propsy" and insert therefor -- propyl --;

Column 1,
Line 11, delete "substitutent" and insert therefor -- substituent --;
Lines 16 and 27, delete "erythernatosus" and insert therefor -- erythematosus --;
Line 61, delete "inunulomodulating" and insert therefor -- immunomodulating --;
Line 62, after "effect" insert -- . --;

Column 3,
Line 17, delete "CE" and insert therefor -- CF --;
Lines 53, 58/60, 62 and 64, delete "dihydro4-hydroxy" and insert therefor
-- dihydro-4-hydroxy --;
Line 65, delete "thiomethyl--methyl" and insert therefor -- thiomethyl-1-methyl --;

Column 4,
Line 5, delete "methylsulphionyl-methyl" and insert therefor
-- methylsulphinyl-1-methyl --;
Line 12, delete "(CAM)" and insert therefor -- EAE --;

Column 5,
Line 39, delete "alklated" and insert therefor -- akylated -- and delete "(E1" and insert therefor -- III --;
Line 40, delete "blown" and insert therefor -- known --;

Column 6,
Lines 17-18, delete "diethylamine" and insert therefor -- triethylamine --;
Line 30, delete "dimethylformamlde" and insert therefor -- dimethylformaldehyde --;
Line 33, delete "1 h" and insert therefor -- 1 M --;
Line 39, delete "(0" and insert therefor -- (10 --;
Line 44, after "days" insert -- . --;
Line 54, after "water" insert -- . --;
Line 55, delete "tehydrofuran" and insert therefor -- tetrahydrofuran --;

UNITED STATES PATENT AND TRADEMARK OFFICE
CERTIFICATE OF CORRECTION

PATENT NO. : 6,121,287
DATED : September 19, 2000
INVENTOR(S) : Bjork et al.

It is certified that error appears in the above-identified patent and that said Letters Patent is hereby corrected as shown below:

Column 7,
Line 14, after "hours" insert -- . --;
Line 51, delete "4methoxy" and insert therefor -- 4-methoxy --;
Line 52, after "carboxamide," insert a new paragraph with "1H";

Column 8,
Line 22, delete "I,$^2$" and insert therefor -- 1,2 --;
Line 31, delete "thiomethyl-" and insert therefor -- thiomethyl-1 --;
Line 31, delete "trimethylamine" and insert therefor -- triethylamine --;
Line 57, delete "thiomethyl-methyl" and insert therefor -- thiomethyl-1-methyl --;

Column 9,
Line 1, delete "1, 2-dihydro4-" and insert therefor -- 1,2-dihydro-4- --;
Line 13, delete "STUN" and insert therefor -- SLJ/N --;
Line 14, delete "C57BV6" and insert therefor -- C57B1/6 --;
Line 35, delete "11" and insert therefor -- II --;
Line 36, delete "4g" and insert therefor -- µg --;
Line 45, delete "metatusophalangeal" and insert therefor -- metatarsophalangeal --;
Line 50, delete "C57B31 6" and insert therefor -- C58B1/6 --;
Line 63, delete "monocyteslalveolar" and insert therefor -- monocytes/alveolar --;
Line 64, delete "Eosinopbil" and insert -- Eosinophil --;
Line 67, delete "tetrahydrochioride" and insert therefor -- tetrahydrochloride --;

Column 10,
Line 11, delete "errocyte" and insert therefor -- erythrocyte --;
Line 20, delete "guinoline3-" and insert therefor -- quinoline-3- --;
Line 21, delete "2,4difluoro" and insert therefor -- 2,4-difluoro --;
Line 56, delete "Chuhill" and insert therefor -- Churchill --;

Column 11,
Line 20, delete "Grissell" and insert therefor -- Grimsell --;
Line 21, delete "Polyarthritis" and insert therefor -- Polyarteritis --;
Line 40, delete "croup" and insert therefor -- group -- and delete "ME" and insert therefor -- Me --;
Line 41, delete "Du" and insert therefor -- Bu --;

UNITED STATES PATENT AND TRADEMARK OFFICE
CERTIFICATE OF CORRECTION

PATENT NO.   : 6,121,287
DATED        : September 19, 2000
INVENTOR(S)  : Bjork et al.

It is certified that error appears in the above-identified patent and that said Letters Patent is hereby corrected as shown below:

Column 12,
Line 4, delete "thiomethyl-4" and insert therefor -- thiomethyl-1- --;
Line 21, delete "compressing an" and insert therefor -- comprising as an --;
Line 64, delete "(iMi)" and insert therefor -- (III) --;

Column 13,
Line 47, delete "ME" and insert therefor -- Me --;

Column 14,
Line 14, delete "dihydro4" and insert therefor -- dihydro-4" --.

Signed and Sealed this

Sixth Day of May, 2003

JAMES E. ROGAN
*Director of the United States Patent and Trademark Office*